(12) United States Patent
Gjerdingen et al.

(10) Patent No.: US 7,217,391 B2
(45) Date of Patent: May 15, 2007

(54) ROTARY INCUBATION STATION FOR IMMUNOASSAY SYSTEMS

(75) Inventors: Donald J. Gjerdingen, Mayer, MN (US); Humayun Qureshi, Eden Prairie, MN (US); Peter G. Werness, Carver, MN (US); Brian D. Wilson, Chaska, MN (US); Mark J. Kittock, Eden Prairie, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 399 days.

(21) Appl. No.: 09/811,028

(22) Filed: Mar. 16, 2001

(65) Prior Publication Data
US 2002/0131895 A1 Sep. 19, 2002

(51) Int. Cl.
*G01N 35/00* (2006.01)
(52) U.S. Cl. .......................................... 422/64; 422/65
(58) Field of Classification Search .................. 422/64, 422/65; 435/809
See application file for complete search history.

(56) References Cited

U.S. PATENT DOCUMENTS

| | | | |
|---|---|---|---|
| 3,787,185 A | 1/1974 | Rohrbaugh et al. ........... 23/253 |
| 4,219,529 A | 8/1980 | Tersteeg et al. .............. 422/65 |
| 4,250,266 A | 2/1981 | Wade ......................... 435/289 |
| 4,906,433 A * | 3/1990 | Minekane ..................... 422/64 |
| 5,075,079 A * | 12/1991 | Kerr et al. .................... 422/64 |
| 5,089,418 A * | 2/1992 | Shaw et al. ................... 436/46 |
| 5,104,807 A | 4/1992 | Mitsumaki et al. ........... 436/47 |
| 5,192,506 A | 3/1993 | Kureshy et al. .............. 422/64 |
| 5,200,151 A | 4/1993 | Long .......................... 422/100 |
| 5,207,987 A | 5/1993 | Kureshy et al. .............. 422/67 |
| 5,244,633 A * | 9/1993 | Jakubowicz et al. .......... 422/64 |
| 5,246,665 A | 9/1993 | Tyranski et al. .............. 422/64 |
| 5,294,404 A | 3/1994 | Grandone et al. ............. 422/64 |
| 5,320,809 A | 6/1994 | Dunn et al. ................... 422/64 |
| 5,324,481 A | 6/1994 | Dunn et al. ................... 422/64 |
| 5,374,395 A | 12/1994 | Robinson et al. ............. 422/64 |
| 5,599,501 A | 2/1997 | Carey et al. ................... 422/64 |
| 5,885,529 A | 3/1999 | Babson et al. ................ 422/65 |
| 5,885,530 A | 3/1999 | Babson et al. ................ 422/65 |
| 5,985,672 A | 11/1999 | Kegelman et al. ............ 436/50 |
| 6,096,272 A | 8/2000 | Clark et al. ................... 422/64 |
| 6,096,561 A | 8/2000 | Tayi ............................ 436/518 |
| 6,190,617 B1 | 2/2001 | Clark et al. .................. 422/104 |

FOREIGN PATENT DOCUMENTS

| | | |
|---|---|---|
| EP | 0 289 789 A1 | 4/1988 |
| EP | 0 571 032 A1 | 5/1993 |

* cited by examiner

*Primary Examiner*—Jill Warden
(74) *Attorney, Agent, or Firm*—Hogan & Hartson LLP

(57) ABSTRACT

A rotary incubation station for an automated analyzer is provided. The rotary incubation station includes a platform, a circular ring-shaped outside rotary wheel having a plurality of nesting locations for washing and reading vessels, and a circular disc-shaped inside rotary wheel having a plurality of nesting locations for incubation and storage of vessels. The rotary incubation station also includes a spur gear mechanism for rotating the outside and inside rotary wheels, including spur gear drivers respectively engaged with spur gear teeth of the outside and inside rotary wheel, providing accurate control of the rotation of the outside and inside rotary wheels.

24 Claims, 6 Drawing Sheets

ROTARY INCUBATION STATION FOR IMMUNOASSAY SYSTEMS

BACKGROUND OF THE INVENTION

1. Area of the Art

The invention relates generally to automated chemical analyzers, and specifically to an incubation station for automated chemical analyzers.

2. Description of the Prior Art

Immunodiagnostic instruments are widely used in clinical chemistry sampling and analyzing applications, and often involving the incubation process for performing various assays. In conventional immunoassay systems, rotary incubation wheels have been introduced. However, most prior art rotation incubation wheels are rotated by a center pivot shaft. These center pivot wheels are usually driven by timing belts. This conventional design often creates timing belt tension problems and/or belt-wear problems. In addition, it often causes problems with outside edge support when any form of pressure is applied.

A further problem with conventional rotary incubation stations is that the reaction vessels are dragged in machined grooves that are semi-rectangular shaped. However, whenever a reaction vessel is dragged over any type of a transition, the reaction vessel can bounce, which causes splashing of the contents inside the reaction vessel. Therefore, the transition areas have to be tightly controlled.

Other problems of conventional incubation stations include limited staging areas, complicated designs, and limited accessibility.

Therefore, it is desirable to provide a new rotary incubation station that overcomes the problems of the conventional incubation stations and provides advantageous features for the incubation process of the automated assays.

SUMMARY OF THE INVENTION

It is an object of the present invention to provide a novel and unique rotary incubation station for automated chemical analyzers, such as an immunodiagnostic instrument.

The objects and advantages of the present invention are achieved in a rotary incubation station of the present invention by implementing a unique design of a spur gear-driven two-wheel design. The rotary incubation station of the present invention has two rotary wheels. The primary wheel is an incubation and storage wheel. The secondary wheel is a wash and read wheel.

The incubation and storage wheel has multiple nesting positions for vessels, and utilizes a spur gear as a driving mechanism. The wheel is positioned horizontally by fixed position bearings to make sure that the wheel is located in the same location after removal and replacement. The horizontal tensioner applies spring-loaded tension on the wheel so that it nests on the fixed horizontal position bearings.

The incubation and storage wheel is further stabilized and positioned in the vertical direction by vertical pressure bearings. Pressure is applied to the wheel with a spring-loaded thrust washer that is part of the station cover.

The wash and read wheel has a similar driving and bearing arrangement as the incubation and storage wheel, except it rotates in a clockwise direction with a different timing. Both wheels are very easy to remove vertically since only the horizontal tension-bearing assemblies contain the wheels.

In summary, the rotary incubation station of the present invention includes a generally circular ring-shaped outside rotary wheel positioned on a stationary platform and having a plurality of nesting locations for washing and reading vessels, and a generally circular disc-shaped inside rotary wheel positioned on the platform inside the outside rotary wheel and having a plurality of nesting locations for the incubation and storage of vessels. The rotary incubation station utilizes spur gear mechanisms for rotating the outside and inside rotary wheels, allowing accurate control of the respective rotation of the outside and inside rotary wheels.

Such an arrangement has been found to provide a number of advantages. As explained in greater detail below, the rotary incubation station of the present invention utilizes spur gear driven wheels which have a positive non-flexing drive motion. The two-wheel design of the incubation station of the present invention also creates a very compact area for incubation storage, which requires less surface area for thermal control. The rotary wheel design also provides fast access, because the incubation and storage wheel needs only to rotate limited degrees for full access of the vessels stored on the wheel.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawing(s). The(se) drawing(s) depict(s) only a typical embodiment of the invention and do not therefore limit its scope. The drawing(s) serve to add specificity and detail, in which.

DETAILED DESCRIPTION OF THE INVENTION

The present invention is directed to a new incubation station used in conjunction with an automated chemical analyzer such as an immunodiagnostic instrument. The incubation station performs the tasks of incubating, reading, and washing vessels as part of the assay process.

Figure 1A:
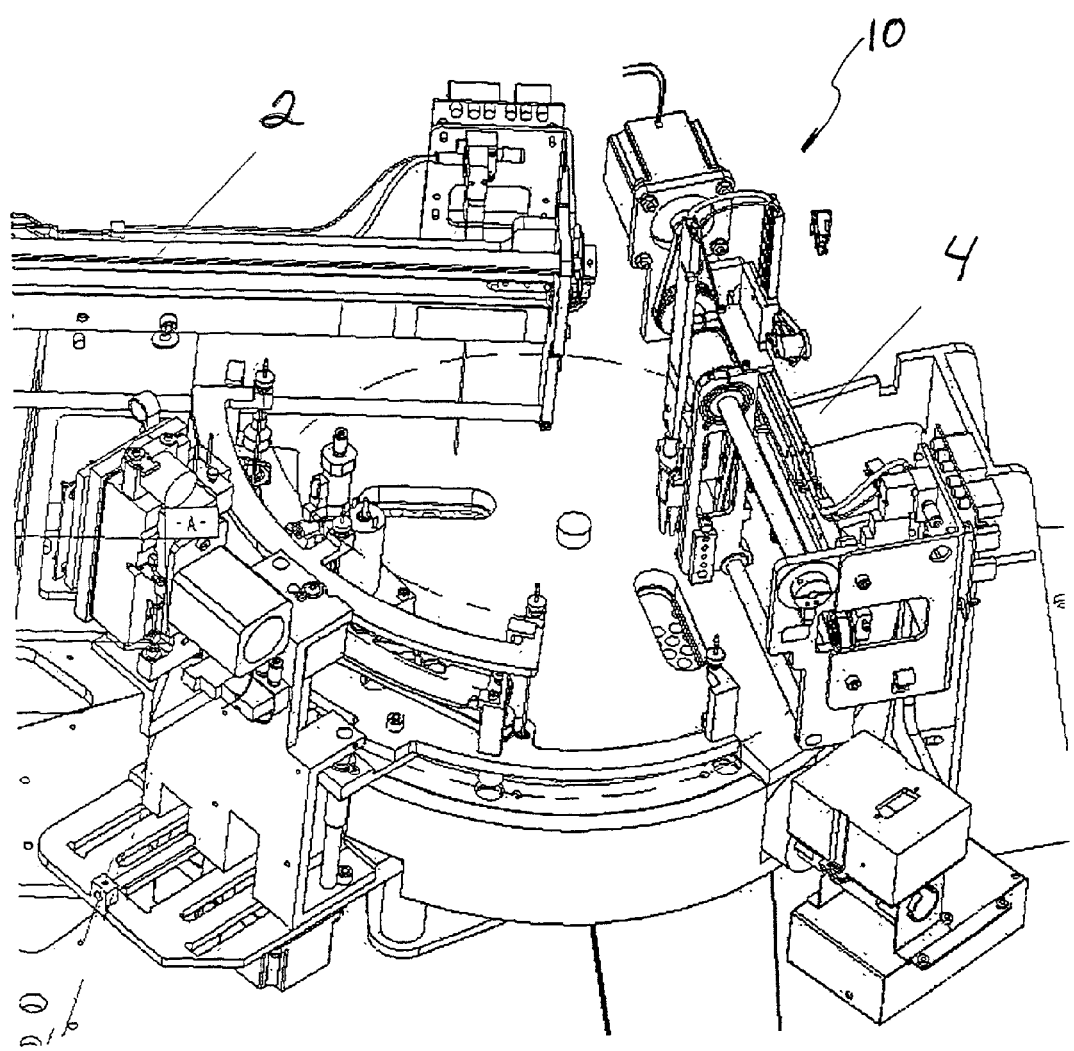
FIG. 1A is an illustrative perspective view of relevant portions of an automatic chemical analyzer, showing the incubation station of the present invention and two pick and place assemblies.
Figure 1B:
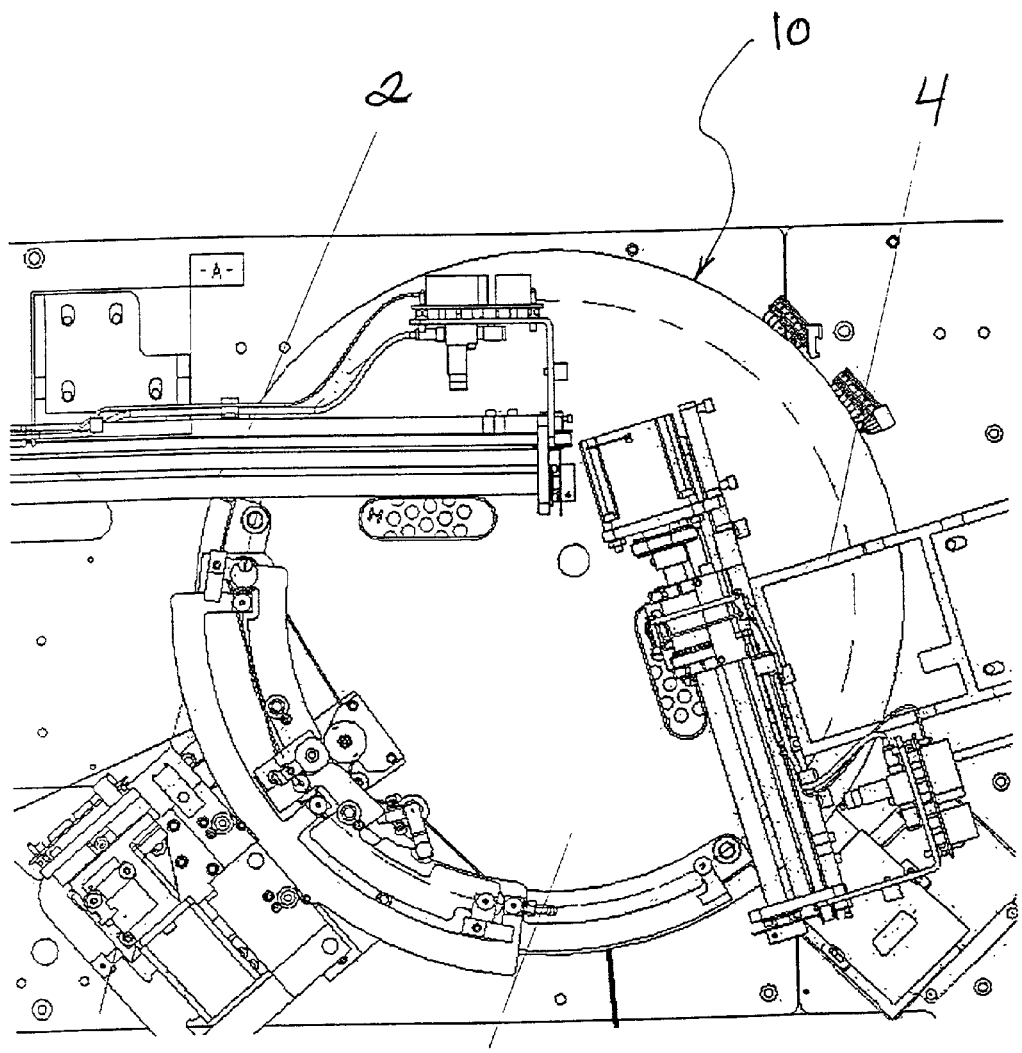
FIG. 1B is an illustrative top view of relevant portions of the automatic chemical analyzer, showing the incubation station of the present invention and two pick and place assemblies.

Referring to FIGS. 1A and 1B, there is shown the incubation station 10 of the present invention which is used as a functional part of an automatic chemical analyzer, showing the incubation station 10 and two pick and place assemblies 2 and 4. The pick and place assembly 2 is an incubator pick and place assembly, and the pick and place assembly 4 is a wash pick and place assembly.

Figure 2A:
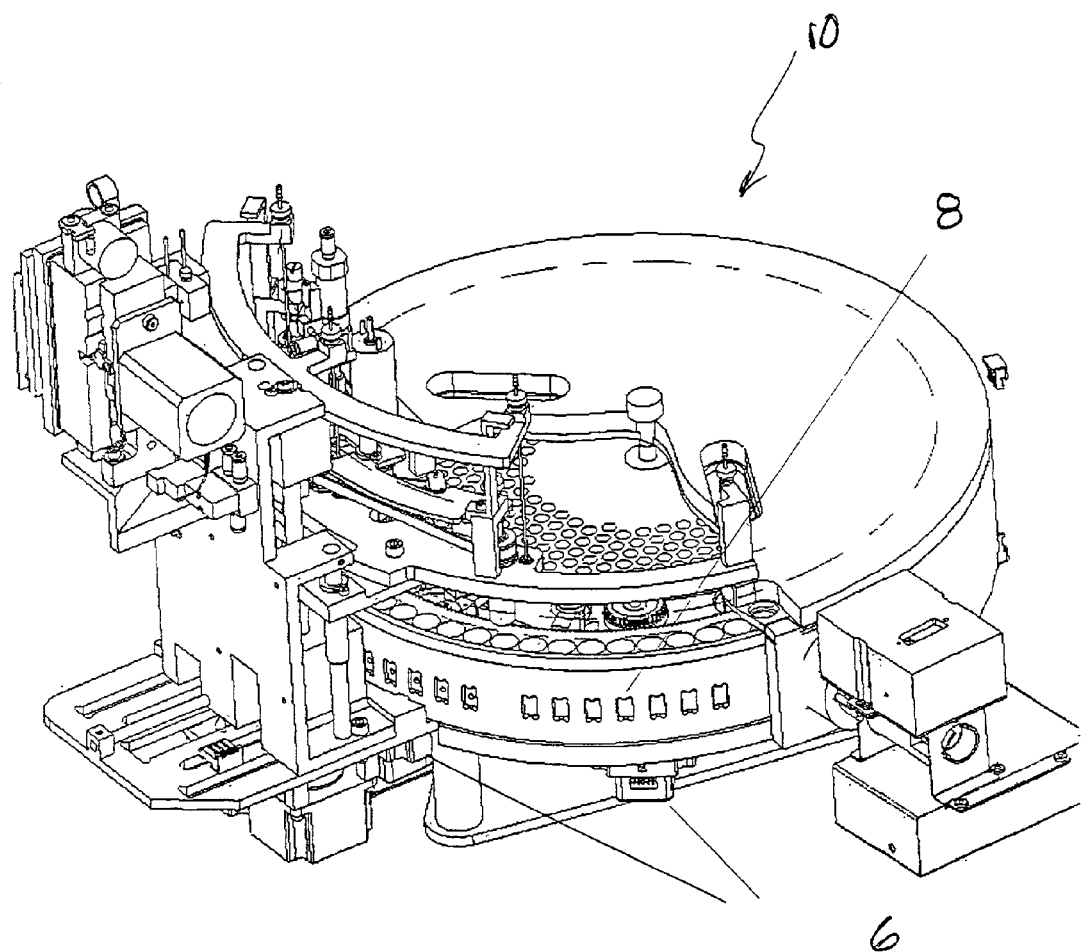
FIG. 2A is an illustrative perspective view of a preferred embodiment of the incubation station of the present invention with encoders and magnets.
Figure 2B:
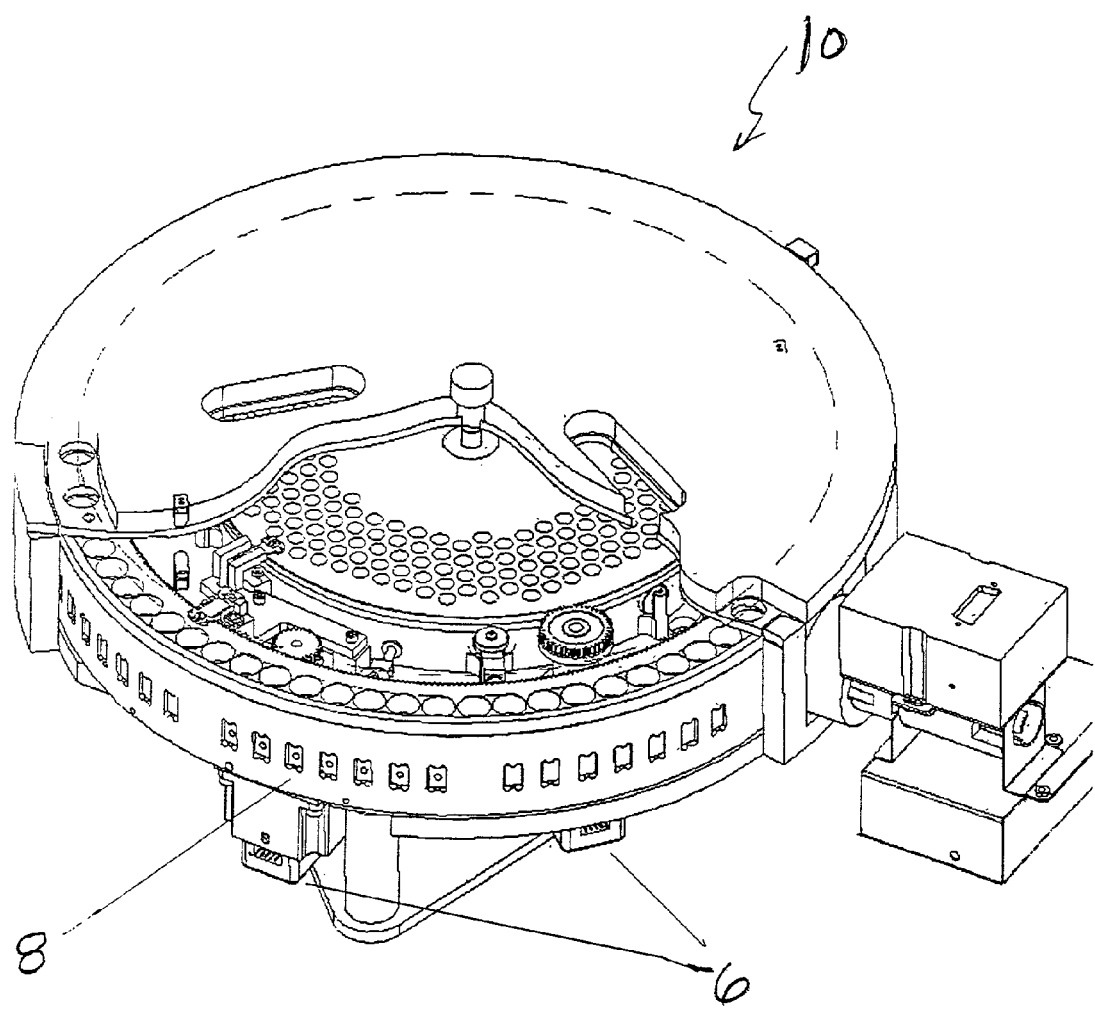
FIG. 2B is an illustrative isolated perspective view of the preferred embodiment of the incubation station of the present invention.

Referring to FIGS. 2A and 2B, there is shown a preferred embodiment of the incubation station 10 of the present invention, with its top cover partially cut-away, also showing the relative locations of the motor with encoder units 6 and magnets 8.

Figure 3:
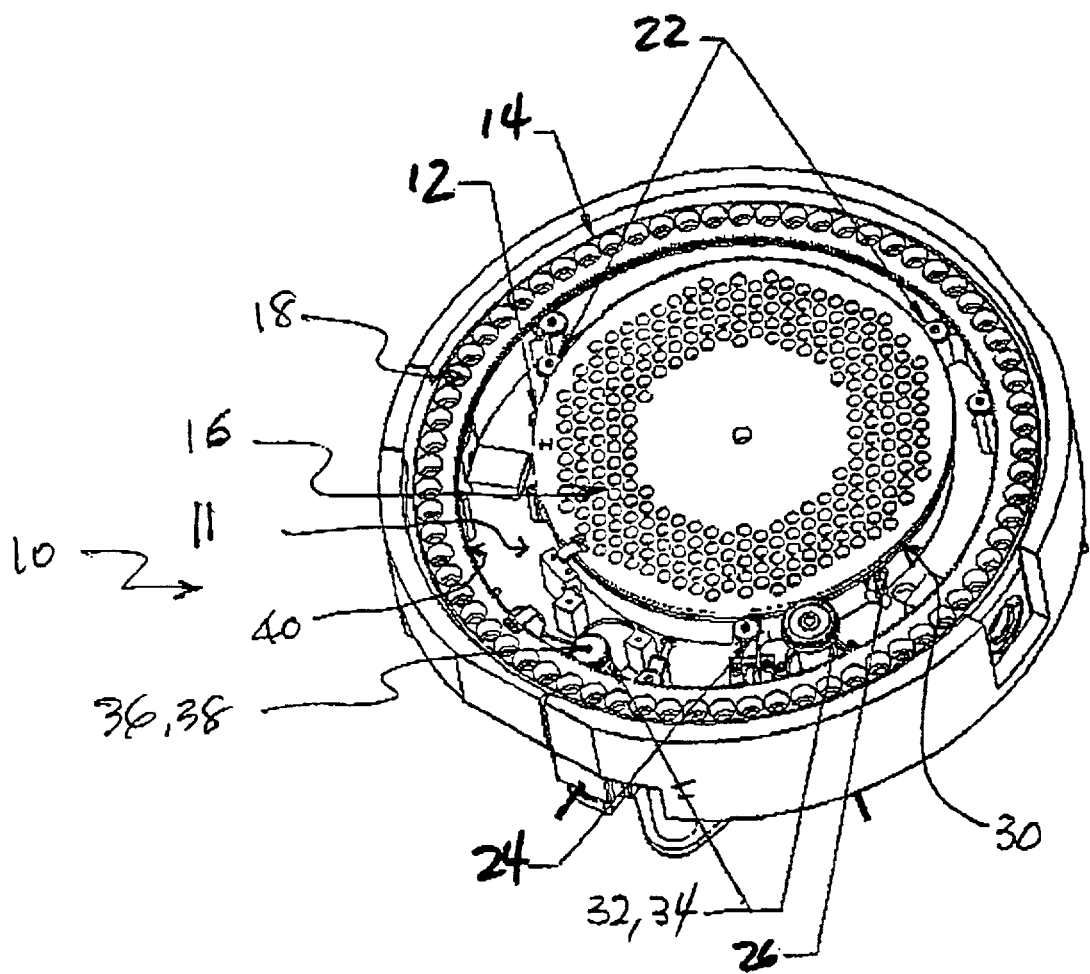
FIG. 3 is an illustrative isolated perspective view of the incubation station of the present invention, with its cover removed to show the two rotary wheels.

Referring to FIG. 3, the incubation station 10 is a rotary station having a generally circular-shaped platform 11 for supporting two rotary incubation wheels: a generally circular disc-shaped inside wheel 12 which is an incubation and storage wheel, and a generally circular ring-shaped outside wheel 14 which is a wash and read wheel. The two pick and place assemblies 2 and 4 are also used for transferring vessels between the inside wheel 12 and the outside wheel 14 of the incubation station 10.

The inside incubation and storage wheel 12 has a multiplicity of densely populated nesting locations 16 for holding vessels. These multiplicity of nesting locations 16 can be randomly accessed by the two pick and place assemblies 2 and 4 with only a limited rotation of the inside wheel 12. In fact, when the two pick and place assemblies 2 and 4 are oppositely positioned, the inside wheel 12 only needs to be rotated a maximum of 180 degrees to have any one of the multiplicity of nesting locations 16 accessed by one of the two pick and place assemblies 2 and 4.

Similarly, the outside wash and read wheel 14 also has a multiplicity of nesting locations 18 for holding vessels, which again can be randomly accessed by the two pick and place assemblies 2 and 4 with only a limited rotation of the outside wheel 14. The nesting locations 18 on the wash and read wheel 14 are designed to minimize the light leakage between these nesting locations 18.

Figure 4:
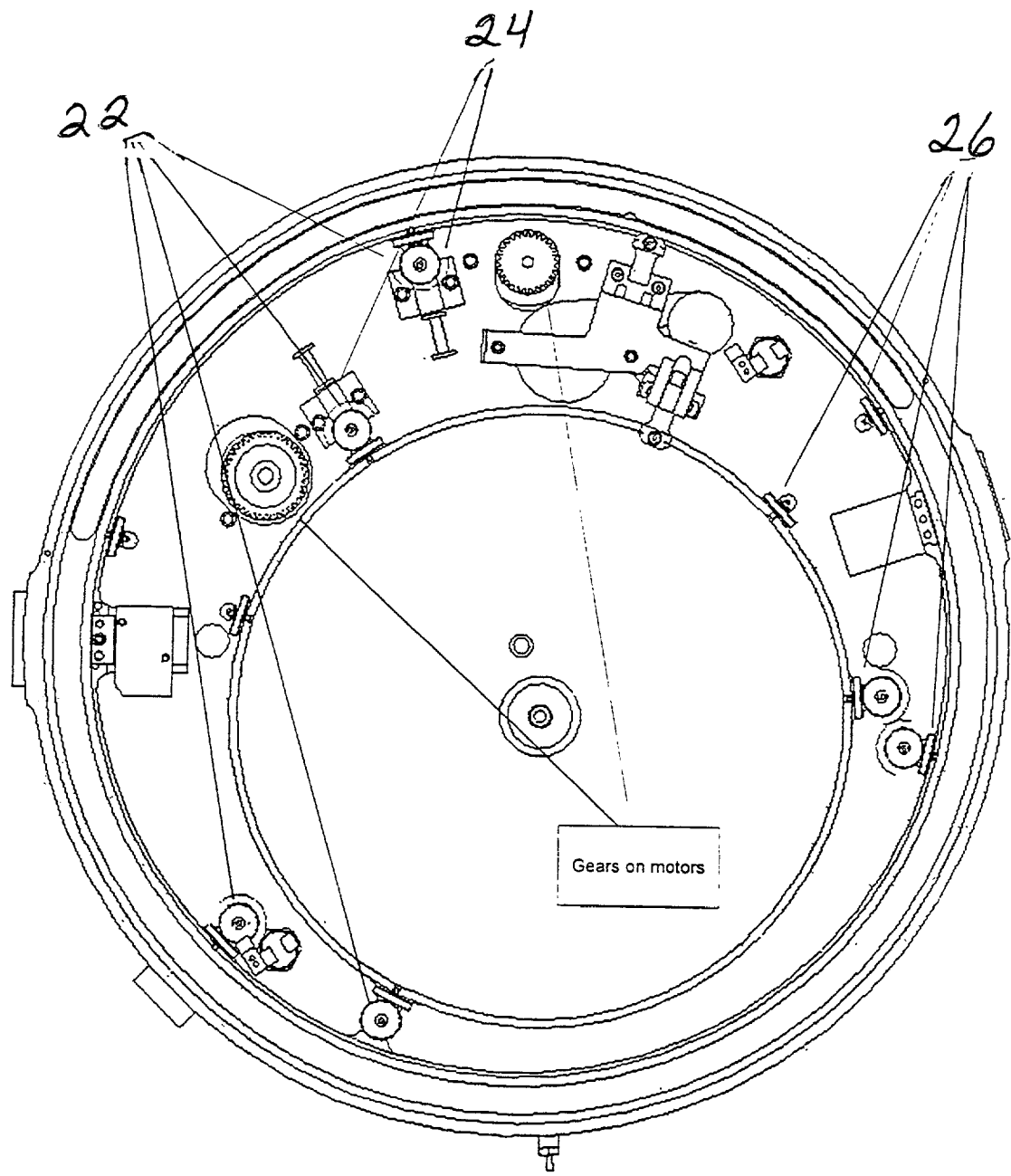
FIG. 4 is an illustrative isolated top view of the incubation station of the present invention, with both wheels removed to show the locations of the horizontal bearings and tensioners, vertical bearings, spur gears, and stepper motors.

Referring to FIG. 4, there is shown the incubation station 10 of the present invention, with both the inside wheel 12 and the outside wheel 14 removed to show the locations of the horizontal bearings and tensioners, vertical bearings, spur gears, and stepper motors on the station platform 11.

The inside incubation and storage wheel 12 is positioned horizontally by several fixed horizontal position bearings 22 to make sure that the inside wheel 12 is located in the same location after removal or replacement. One or more horizontal tensioners 24 are provided to apply spring-loaded tension on the inside wheel 12 so that it nests on the fixed horizontal position bearings.

The inside wheel 12 is further positioned vertically by a plurality of vertical pressure bearings 26 which position the inside wheel 12 in the vertical direction and give stability to the inside wheel 12.

In addition, downward pressure is applied to the inside wheel 12 by a spring-loaded thrust washer that is part of the incubation station cover (not shown).

The two wheels 12 and 14 of the incubation station 10 of the present invention are driven by spur gear driving mechanism. The inside wheel 12 has spur gear teeth 30 on its outer periphery which are engaged with a spur gear driver 32 with a pitch diameter spacer for proper gear mating. A smooth surface diameter below the spur gear teeth is used as a bearing surface and a spacing surface to set the proper mating pitch diameter contact for the spur gear driver 32. The inside wheel 12 is driven by the spur gear driver 32 which, in turn, is driven by a rotary actuator 34, such as a stepper motor, with an add-on encoder for positioning.

The outside wash and read wheel 14 has a similar driving arrangement as the inside incubation and storage wheel 14. The outside wheel 14 has spur gear teeth 40 on its inner periphery which are engaged with a spur gear driver 36, which, in turn, is driven by a rotary actuator 38, such as a stepper motor, except it rotates in a direction opposite to that of the inside wheel 12 and also with a different timing.

Described generally, the present invention is a rotary incubation station of an automated analyzer, comprising: (a) a generally circular-shaped platform; (b) a generally circular ring-shaped outside rotary wheel having a plurality of nesting locations for washing and reading vessels and a plurality of spur gear teeth on its inner periphery; (c) means for positioning the outside rotary wheel on the platform adjacent to its periphery, allowing the outside rotary wheel to rotate about a first axis; (d) a generally circular disc-shaped inside rotary wheel having a plurality of nesting locations for incubation and storage of vessels and a plurality of spur gear teeth on its outer periphery; (e) means for positioning the inside rotary wheel on the platform inside the outside rotary wheel, allowing the inside rotary wheel to rotate about a second axis; (f) means for rotating the outside rotary wheel, including a first spur gear driver engaged with the spur gear teeth of the outside rotary wheel and a first actuator for driving the first spur gear, providing accurate control of the rotation of the outside rotary wheel; and (g) means for rotating the inside rotary wheel independent of the rotation of the outside rotary wheel, including a second spur gear driver engaged with the spur gear teeth of the inside rotary wheel and a first actuator for driving the first spur gear, providing accurate control of the rotation of the inside rotary wheel.

The incubation station of the present invention is provided with the necessary electrical and electronic means for power supply, microprocessor control, and connection with the automated analyzer's main control system for integrated control and operation.

The incubation station of the present invention has many unique and advantageous features, including the two-wheel design that provides a compact arrangement which requires less surface area for thermal control, and adaptable or easily modifiable to adapt to various immunodiagnostic instruments. In addition, the rotary incubation station of the present invention utilizes spur gear driven wheels which have a positive non-flexing drive motion and provides fast access, because the incubation/storage wheel needs only to rotate limited degrees for full access of the vessels stored on the wheel. Furthermore, both the inside and the outside wheels are very easy to remove (vertically), since only the horizontal tension bearing assemblies contain the wheels.

The foregoing is meant to illustrate, but not to limit, the scope of the invention. Indeed, those of ordinary skill in the art can readily envision and produce further embodiments, based on the teachings herein, without undue experimentation. Suitable materials are commercially available and would be known to those of ordinary skill in the art in view of this disclosure.

It is to be understood that the form of the device depicted in the figures has been chosen only for the purpose of describing a particular embodiment and function of the invention, and that the material of the invention can be addressed in various ways and incorporated in other types of devices, all of which will be evident to those working in the art.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A rotary incubation station of an automated analyzer, comprising:
    a. a platform;
    b. a generally circular ring-shaped outside rotary wheel having a plurality of nesting locations for washing and reading vessels;
    c. means for positioning said outside rotary wheel on said platform, allowing said outside rotary wheel to rotate;
    d. a generally circular disc-shaped inside rotary wheel having a plurality of nesting locations for incubation and storage of said vessels;
    e. means for positioning said inside rotary wheel on said platform inside said outside rotary wheel, allowing said inside rotary wheel to rotate;
    f. first spur gear mechanism for rotating said outside rotary wheel including a plurality of spur gear teeth on the inner periphery of the outside rotary wheel, wherein the first spur gear means allows accurate control of the rotation of said outside rotary wheel;
    g. second spur gear mechanism for rotating said inside rotary wheel independent of the rotation of said outside rotary wheel, the second spur gear mechanism comprising a plurality of spur gear teeth on the outer periphery of the inside rotary wheel and allowing accurate control of the rotation of said inside rotary wheel; and
    h. two pick and place assemblies assembly for transferring said vessels between the inside rotary wheel and outside rotary wheel.

2. The rotary incubation station as defined in claim 1, wherein said means for positioning said inside rotary wheel comprises a plurality of horizontal bearings for positioning said inside rotary wheel inside said outside rotary wheel.

3. The rotary incubation station as defined in claim 2, wherein said means for positioning said inside rotary wheel further comprises at least one horizontal tensioner for locating said inside rotary wheel inside said outside rotary wheel.

4. The rotary incubation station as defined in claim 1, wherein said means for positioning said inside rotary wheel comprises a plurality of vertical pressure bearings for rotatably supporting said inside rotary wheel on said platform.

5. The rotary incubation station as defined in claim 1, wherein said first spur gear means for rotating said outside rotary wheel comprises a plurality of spur gear teeth on an inner periphery of said outside rotary wheel, and a first spur gear driver engaged with said spur gear teeth of said outside rotary wheel.

6. The rotary incubation station as defined in claim 5, wherein said first spur gear means for rotating said outside rotary wheel further comprises a first rotary actuator for driving said first spur gear driver.

7. The rotary incubation station as defined in claim 6, wherein said first rotary actuator is an electrical stepper motor.

8. The rotary incubation station as defined in claim 1, wherein said second spur gear means for rotating said inside rotary wheel comprises a plurality of spur gear teeth on an outer periphery of said inside rotary wheel, and a second spur gear driver engaged with said spur gear teeth of said inside rotary wheel.

9. The rotary incubation station as defined in claim 8, wherein said second spur gear means for rotating said inside rotary wheel further comprises a second rotary actuator for driving said second spur gear driver.

10. The rotary incubation station as defined in claim 9, wherein said second rotary actuator is an electrical stepper motor.

11. A rotary incubation station of an automated analyzer, comprising:
    a. a generally circular-shaped platform;
    b. a generally circular ring-shaped outside rotary wheel having a plurality of nesting locations for washing and reading vessels and a plurality of spur gear teeth on its inner periphery;
    c. means for positioning said outside rotary wheel on said platform adjacent to its periphery, allowing said outside rotary wheel to rotate about a first axis;
    d. a generally circular disc-shaped inside rotary wheel having a plurality of nesting locations for incubation and storage of said vessels and a plurality of spur gear teeth on its outer periphery;
    e. means for positioning said inside rotary wheel on said platform inside said outside rotary wheel, allowing said inside rotary wheel to rotate about a second axis;
    f. means for rotating said outside rotary wheel, including a first spur gear driver engaged with said spur gear teeth of said outside rotary wheel, providing accurate control of the rotation of said outside rotary wheel;
    g. means for rotating said inside rotary wheel independent of the rotation of said outside rotary wheel, including a second spur gear driver engaged with said spur gear teeth of said inside rotary wheel, providing accurate control of the rotation of said inside rotary wheel; and
    h. two pick and place assemblies for transferring said vessels between the inside rotary wheel and outside rotary wheel.

12. The rotary incubation station as defined in claim 11, wherein said means for positioning said inside rotary wheel comprises a plurality of horizontal bearings for positioning said inside rotary wheel inside said outside rotary wheel.

13. The rotary incubation station as defined in claim 12, wherein said means for positioning said inside rotary wheel further comprises at least one horizontal tensioner for locating said inside rotary wheel inside said outside rotary wheel.

14. The rotary incubation station as defined in claim 11, wherein said means for positioning said inside rotary wheel comprises a plurality of vertical pressure bearings for rotatably supporting said inside rotary wheel on said platform.

15. The rotary incubation station as defined in claim 11, wherein said means for rotating said outside rotary wheel comprises a first rotary actuator for driving said first spur gear driver.

16. The rotary incubation station as defined in claim 15, wherein said first rotary actuator is an electrical stepper motor.

17. The rotary incubation station as defined in claim 11, wherein said means for rotating said inside rotary wheel comprises a second rotary actuator for driving said second spur gear driver.

18. The rotary incubation station as defined in claim 17, wherein said second rotary actuator is an electrical stepper motor.

19. A rotary incubation station of an automated analyzer, comprising:
    a. a generally circular-shaped platform;
    b. a generally circular ring-shaped outside rotary wheel having a plurality of nesting locations for washing and reading vessels and a plurality of spur gear teeth on its inner periphery;

c. means for positioning said outside rotary wheel on said platform adjacent to its periphery, allowing said outside rotary wheel to rotate about a first axis;

d. a generally circular disc-shaped inside rotary wheel having a plurality of nesting locations for incubation and storage of said vessels and a plurality of spur gear teeth on its outer periphery;

e. means for positioning said inside rotary wheel on said platform inside said outside rotary wheel, allowing said inside rotary wheel to rotate about a second axis;

f. means for rotating said outside rotary wheel, including a first spur gear driver engaged with said spur gear teeth of said outside rotary wheel and a first actuator for driving said first spur gear, providing accurate control of the rotation of said outside rotary wheel;

g. means for rotating said inside rotary wheel independent of the rotation of said outside rotary wheel, including a second spur gear driver engaged with said spur gear teeth of said inside rotary wheel and a first actuator for driving said first spur gear, providing accurate control of the rotation of said inside rotary wheel; and h. two pick and place assemblies for transferring said vessels between the inside rotary wheel and outside rotary wheel.

20. The rotary incubation station as defined in claim 19, wherein said means for positioning said inside rotary wheel comprises a plurality of horizontal bearings for positioning said inside rotary wheel inside said outside rotary wheel.

21. The rotary incubation station as defined in claim 20, wherein said means for positioning said inside rotary wheel further comprises at least one horizontal tensioner for locating said inside rotary wheel inside said outside rotary wheel.

22. The rotary incubation station as defined in claim 19, wherein said means for positioning said inside rotary wheel comprises a plurality of vertical pressure bearings for rotatably supporting said inside rotary wheel on said platform.

23. The rotary incubation station as defined in claim 19, wherein said first rotary actuator is an electrical stepper motor.

24. The rotary incubation station as defined in claim 19, wherein said second rotary actuator is an electrical stepper motor.

* * * * *